US010189049B2

(12) United States Patent
Torashima et al.

(10) Patent No.: US 10,189,049 B2
(45) Date of Patent: Jan. 29, 2019

(54) CAPACITIVE TRANSDUCER AND METHOD OF MANUFACTURING SAME

(71) Applicant: CANON KABUSHIKI KAISHA, Tokyo (JP)

(72) Inventors: Kazutoshi Torashima, Yokohama (JP); Kenichi Nagae, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 217 days.

(21) Appl. No.: 14/251,735

(22) Filed: Apr. 14, 2014

(65) Prior Publication Data

US 2014/0318254 A1    Oct. 30, 2014

(30) Foreign Application Priority Data

Apr. 25, 2013  (JP) ................................. 2013-092668
Feb. 7, 2014   (JP) ................................. 2014-022480

(51) Int. Cl.
 | | |
 |---|---|
 | H04R 19/00 | (2006.01) |
 | B06B 1/02 | (2006.01) |
 | G01N 29/24 | (2006.01) |
 | G01N 29/34 | (2006.01) |

(52) U.S. Cl.
CPC ....... B06B 1/0292 (2013.01); G01N 29/2406 (2013.01); G01N 29/2418 (2013.01); G01N 29/34 (2013.01); G01N 2291/045 (2013.01); G01N 2291/101 (2013.01); Y10T 29/49007 (2015.01)

(58) Field of Classification Search
USPC ........................................................ 340/73
See application file for complete search history.

(56) References Cited

U.S. PATENT DOCUMENTS

| | | | |
|---|---|---|---|
| 2,837,728 A | 6/1958 | Schuck .......................... | 367/153 |
| 4,425,525 A | 1/1984 | Smith et al. .................. | 310/336 |
| 4,460,841 A | 7/1984 | Smith et al. .................. | 310/334 |
| 5,488,956 A | 2/1996 | Bartelt et al. ................. | 600/459 |
| 5,870,351 A * | 2/1999 | Ladabaum ............ | B06B 1/0292 |
| | | | 367/163 |

(Continued)

FOREIGN PATENT DOCUMENTS

| | | |
|---|---|---|
| CN | 102015127 | 4/2011 |
| CN | 101883309 | 11/2011 |

(Continued)

OTHER PUBLICATIONS

Drinkwater, Bruce W., and Paul D. Wilcox. "Ultrasonic arrays for non-destructive evaluation: A review." Ndt & E International 39.7 (2006): 525-541.*

(Continued)

*Primary Examiner* — Isam A Alsomiri
*Assistant Examiner* — Jonathan D Armstrong
(74) *Attorney, Agent, or Firm* — Venable LLP

(57) ABSTRACT

A side lobe in a capacitive transducer is reduced. Provided is a capacitive transducer including an element including a plurality of cells supported such that a vibrating membrane including one of a pair of electrodes formed with an gap between the electrodes is capable of vibration, wherein a distance between cells in an end portion of the element is greater than a distance between cells in a middle portion of the element.

12 Claims, 7 Drawing Sheets

(56) References Cited

U.S. PATENT DOCUMENTS

| | | | |
|---|---|---|---|
| 6,359,367 | B1 | 3/2002 | Sumanaweera et al. ...... 310/309 |
| 6,381,197 | B1 * | 4/2002 | Savord ................. B06B 1/0292 367/178 |
| 7,778,113 | B2 | 8/2010 | Machida et al. .............. 367/181 |
| 7,892,176 | B2 * | 2/2011 | Wodnicki ............ A61B 8/0833 257/E27.006 |
| 8,456,958 | B2 | 6/2013 | Felix et al. .................. 367/181 |
| 2005/0075572 | A1 | 4/2005 | Mills et al. .................. 600/459 |
| 2007/0059858 | A1 | 3/2007 | Caronti et al. .................. 438/50 |
| 2008/0259725 | A1 | 10/2008 | Bayram et al. ................... 367/7 |
| 2010/0283354 | A1 | 11/2010 | Soeda .......................... 310/300 |
| 2010/0327380 | A1 | 12/2010 | Chang .......................... 257/419 |
| 2011/0208059 | A1 | 8/2011 | Cerofolini .................... 600/447 |
| 2012/0150012 | A1 | 6/2012 | Fujimoto et al. |
| 2012/0259218 | A1 | 10/2012 | Nagae et al. ................. 600/437 |
| 2013/0255389 | A1 | 10/2013 | Watanabe et al. ............. 73/655 |
| 2014/0010052 | A1 | 1/2014 | Torashima et al. ........... 367/181 |
| 2015/0091477 | A1 | 4/2015 | Kandori et al. ............. 318/116 |

FOREIGN PATENT DOCUMENTS

| | | |
|---|---|---|
| CN | 102458692 | 5/2012 |
| CN | 102596053 A | 7/2012 |
| EP | 0401027 | 12/1990 |
| EP | 2793048 A | 10/2014 |
| GB | 2114857 A | 8/1983 |
| JP | S58-161492 | 9/1983 |
| JP | H01-024479 | 5/1989 |
| JP | H01-024480 | 5/1989 |
| JP | H06-125894 | 5/1994 |
| JP | H07-193896 | 7/1995 |
| JP | 2004-350700 | 12/2004 |
| JP | 2004-350702 | 12/2004 |
| JP | 2004-350703 | 12/2004 |
| JP | 2005-103294 | 4/2005 |
| JP | 2005-117159 | 4/2005 |
| JP | 2008-098697 | 4/2008 |
| JP | 2010-183979 | 8/2010 |
| JP | 2012-217624 | 11/2012 |
| JP | 2012-234208 | 11/2012 |
| JP | 2014-017566 | 1/2014 |
| WO | WO 2010/073534 A1 | 7/2010 |
| WO | WO 2013/032021 A | 3/2013 |

OTHER PUBLICATIONS

Yaralioglu, Goksen G., et al. "Calculation and measurement of electromechanical coupling coefficient of capacitive micromachined ultrasonic transducers." Ultrasonics, Ferroelectrics, and Frequency Control, IEEE Transactions on 50.4 (2003): 449-456.*

Nikoozadeh, Amin, et al. "Analytical calculation of collapse voltage of CMUT membrane [capacitive micromachined ultrasonic transducers]." Ultrasonics Symposium, 2004 IEEE. vol. 1. IEEE, 2004.*
Ergun, Arif S., Goksen G. Yaralioglu, and Butrus T. Khuri-Yakub. "Capacitive micromachined ultrasonic transducers: Theory and technology." Journal of Aerospace Engineering 16.2 (2003): 76-84.*
Lohfink, Annette, and Peter-Christian Eccardt. "Linear and nonlinear equivalent circuit modeling of CMUTs." Ultrasonics, Ferroelectrics, and Frequency Control, IEEE Transactions on 52.12 (2005): 2163-2172.*
Wygant, Ira O., et al. "50 kHz capacitive micromachined ultrasonic transducers for generation of highly directional sound with parametric arrays." Ultrasonics, Ferroelectrics, and Frequency Control, IEEE Transactions on 56.1 (2009): 193-203.*
Nikoozadeh, Amin, and Pierre T. Khuri-Yakub. "CMUT with substrate-embedded springs for non-flexural plate movement." Ultrasonics Symposium (IUS), 2010 IEEE. IEEE, 2010.*
Ergun, A. S., et al. "Capacitive micromachined ultrasonic transducers: fabrication technology." IEEE transactions on ultrasonics, ferroelectrics, and frequency control 52.12 (2005): 2242-2258.*
English Machine Translation ofJP2004350700 (A). Dec. 16, 2004. JP4370120. (B2) Nov. 25, 2009. Adachi Hideo. Sawada Yukihiko. Olympus Corp. May 26, 2003 Priority Date.*
English Machine Translation of JPH07193896. Harutomuuto Baruteruto. Ekeruto Barutoshiyu. Siemens Ag. Sep. 23, 1993 Priority Date. Ultrasonic Wave Converter Array.*
H. Taki et al., "High Range Resolution Medical Acoustic Vascular Imaging with Frequency Domain Interferometry", *Proceedings of 32nd International Conference of the IEEE Engineering in Medicine and Biology Society*, pp. 5298-5301 ( 2010).
U.S. Appl. No. 14/251,743, filed Apr. 14, 2014.
EESR dated May 12, 2015 in counterpart EPA 14163663.9 (in English).
Extended European Search Report dated Aug. 14, 2015 in EPA 14163665.4 (in English).
H. Taki et al., "High Resolution Medical Acoustic Vascular Imaging Using Frequency Domain Interferometry", *Ninth IASTED International Conference on Visualization, Imaging and Image Processing (VIIP 2009)*, pp. 7-12 (Jul. 13, 2009).
Extended European Search Report dated Jun. 2, 2015 in EPA 14163664.7 (in English).
Office Action dated Dec. 23, 2015 in P.R. China patent application 201410180728.7, with translation.
Office Action dated Jan. 13, 2016 in P.R. China patent application 201410171904.0, with translation.
Office Action dated Nov. 21, 2017 in Japanese patent application 2014-022479, with translation.
Office Action dated Nov. 21, 2017 in Japanese patent application 2014-022480, with translation.
Office Action dated Sep. 18, 2018, in counterpart CN 201710112853.8 (8 pages).

* cited by examiner

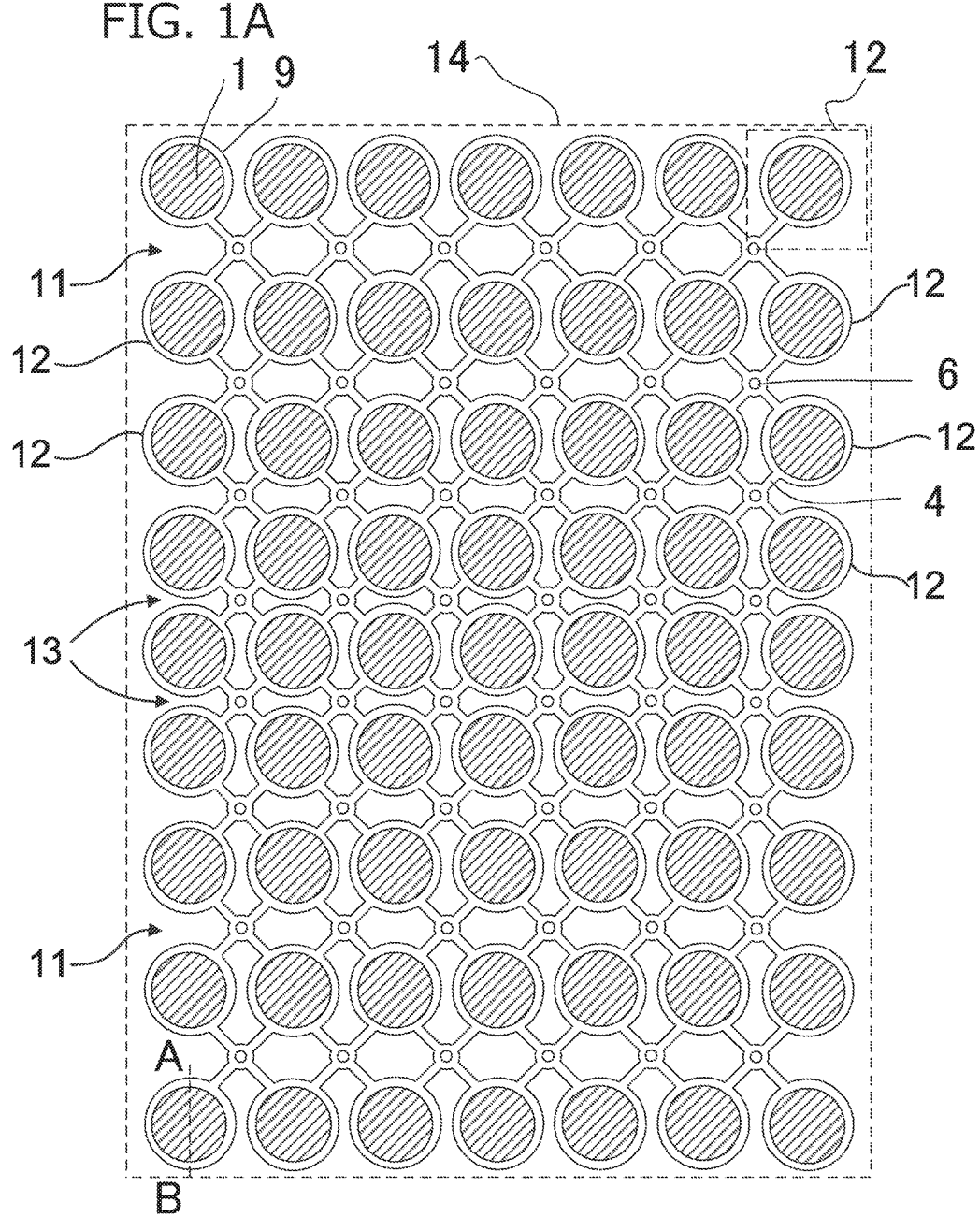

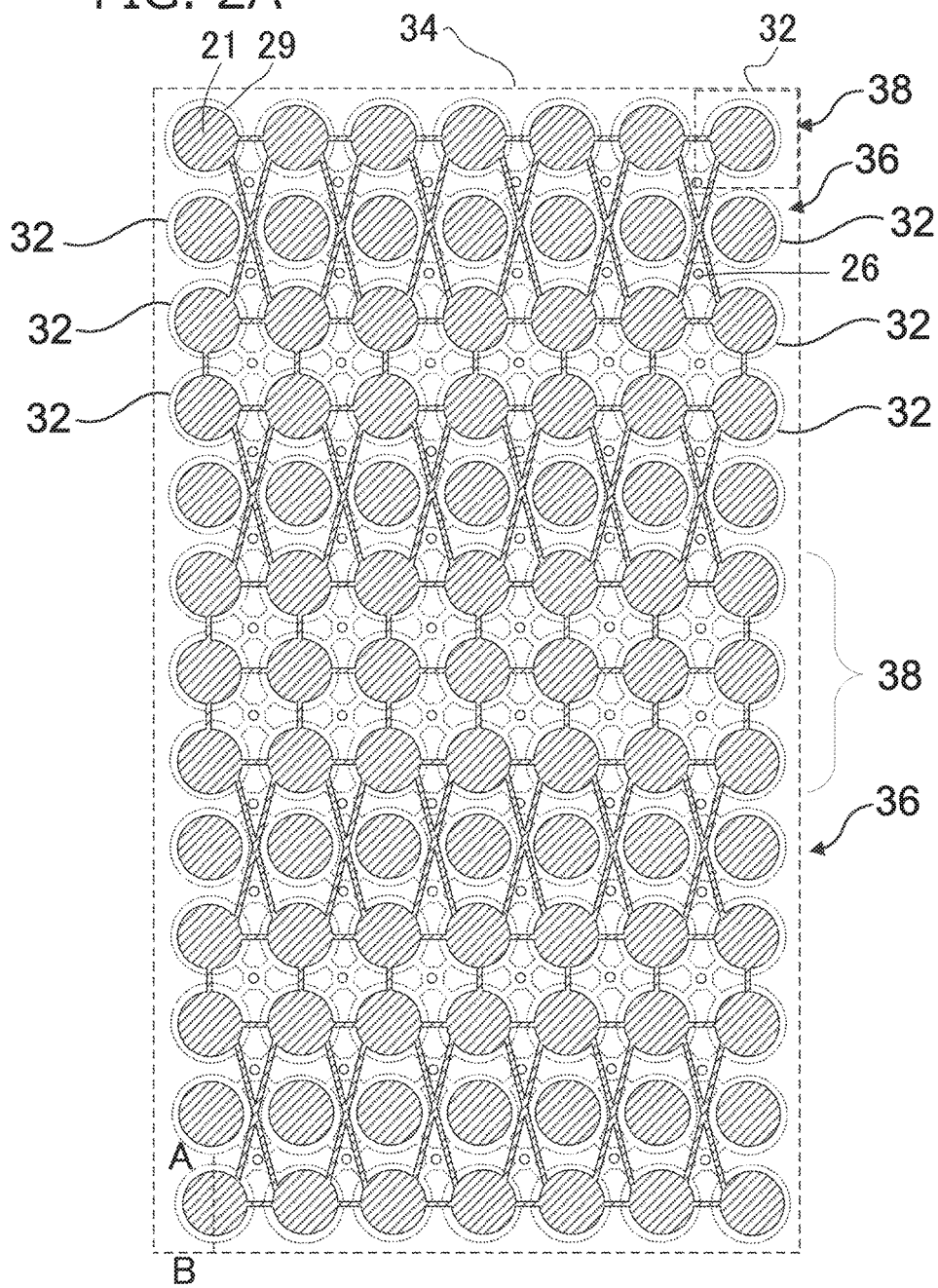

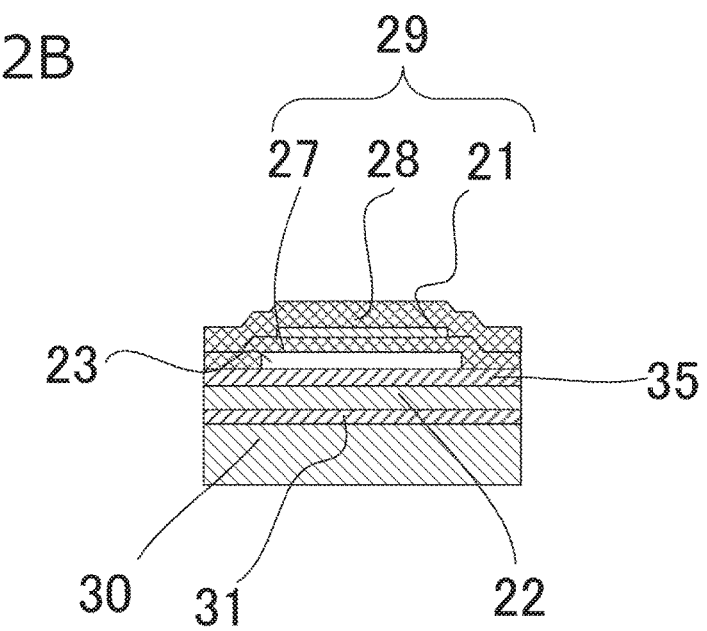

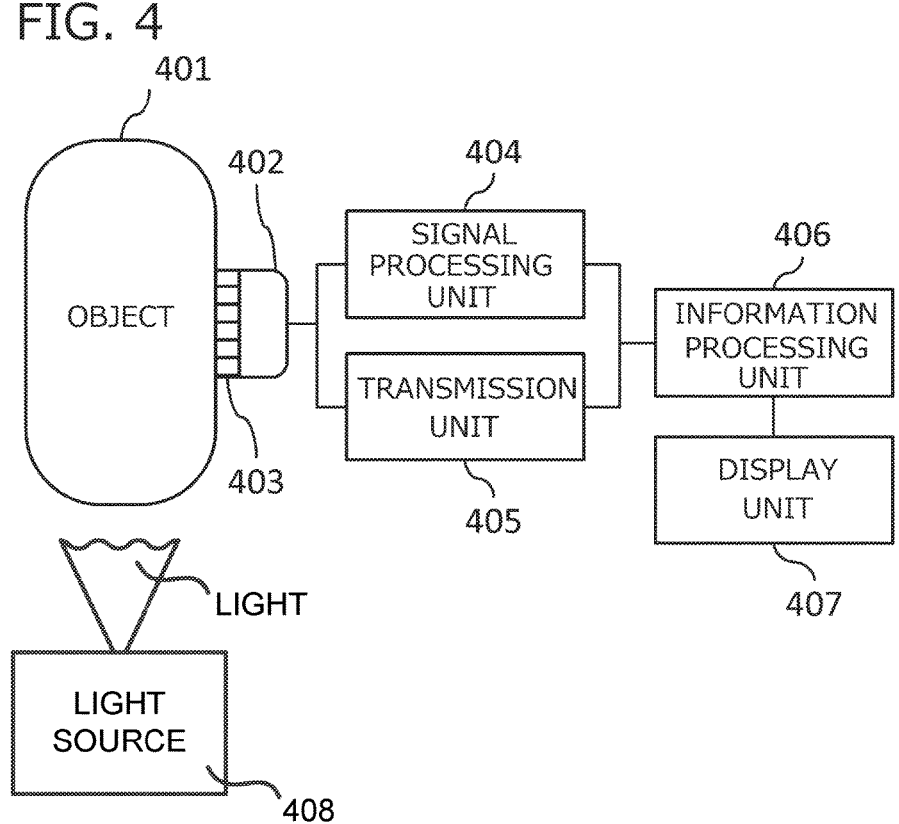

CAPACITIVE TRANSDUCER AND METHOD OF MANUFACTURING SAME

BACKGROUND OF THE INVENTION

Field of the Invention

The present invention relates to a capacitive transducer and a method of manufacturing same.

Description of the Related Art

Conventionally, micromechanical components manufactured by micromachining technology have been processable on a scale on the order of micrometers. Through use thereof, various micro-functional elements have been realized. Capacitive transducers using such technology have been studied as a substitute for piezoelectric elements. With such a capacitive transducer, an ultrasound wave can be transmitted and received using vibration of a vibrating membrane, and excellent wideband characteristics particularly in liquid can be obtained easily.

There is a capacitive transducer including an element in which cells are arranged in a square shape or rectangle shape and the gaps between adjacent cells are uniform (see Japanese Patent Application Laid-open No. 2008-98697). Also, there is a capacitive transducer in which the transmission efficiency or receiving sensitivity of a cell in an end portion of an element is lower than the transmission efficiency or receiving sensitivity of a cell in a middle portion of the element (see U.S. Pat. No. 8,456,958).

Patent Literature 1: Japanese Patent Application Laid-open No. 2008-98697
Patent Literature 2: U.S. Pat. No. 8,456,958

SUMMARY OF THE INVENTION

In the case of transmitting an ultrasound wave with a capacitive transducer including an element in which cells are arranged in a square shape or rectangle shape and gaps between adjacent cells are uniform, the radiated sound pressure is uniform as between an end portion and a middle portion of the element. Therefore, a side lobe in an ultrasound beam produced by the transducer easily occurs. The quality of an ultrasound image using the ultrasound beam may deteriorate due to the side lobe. The image quality may deteriorate in a similar manner in the case of reception as well.

In a capacitive transducer in which the transmission efficiency or receiving sensitivity of a cell in an end portion of an element is lower than in a middle portion, the structure is such that the shape of a cell in the end portion of the element and the shape of a cell in the middle portion of the element differ. With this configuration, apodization by which a side lobe is reduced is possible. Therefore, an ultrasound wave in an unnecessary frequency band may be transmitted or received at the time of transmitting or receiving an ultrasound wave, which deteriorates the S/N ratio.

The present invention has been made based on recognition of such a task. An object of the present invention is to reduce a side lobe in a capacitive transducer.

The present invention provides a capacitive transducer comprising:
an element including a plurality of cells supported such that a vibrating membrane including one of a pair of electrodes formed with an gap inbetween is capable of vibration, wherein
a distance between cells in an end portion of the element is greater than a distance between cells in a middle portion of the element.

The present invention also provides a method of manufacturing a capacitive transducer including an element including a plurality of cells,
the method comprising the steps of:
forming a plurality of first electrodes; and
forming a vibrating membrane capable of vibration and including a plurality of second electrodes paired with the plurality of first electrodes respectively to thereby form a plurality of the cells including a pair of the first electrode and the second electrode, wherein
a distance between cells in an end portion of the element is made greater than a distance between cells in a middle portion of the element in the step of formation.

With the present invention, a side lobe in a capacitive transducer can be reduced.

Further features of the present invention will become apparent from the following description of exemplary embodiments with reference to the attached drawings.

BRIEF DESCRIPTION OF THE DRAWINGS

FIG. 1A is a top view of a capacitive transducer in Example 1;
FIG. 2A is a top view of a capacitive transducer in Example 2;
FIG. 2B is a sectional view along line A-B of the capacitive transducer in Example 2;
FIG. 4 is a block diagram illustrating the configuration of an object information acquiring apparatus.

DESCRIPTION OF THE EMBODIMENTS

Figure 1B:
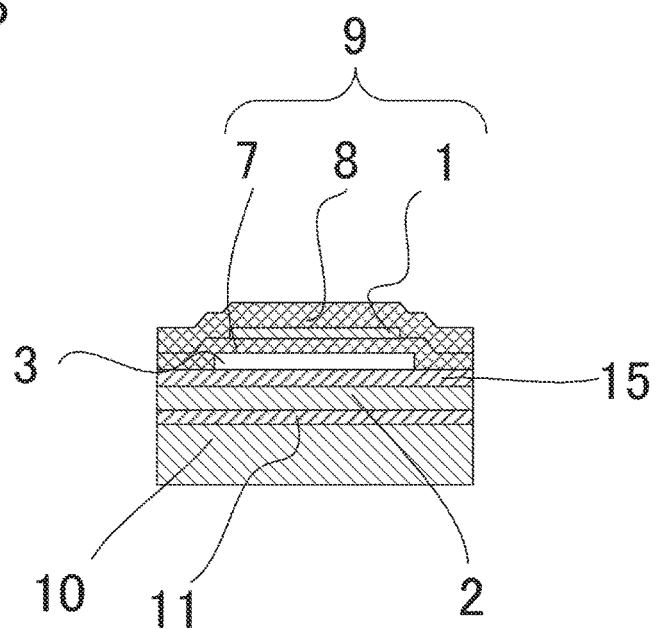
FIG. 1B is a sectional view along line A-B of the capacitive transducer in Example 1.

A preferred embodiment of the present invention will be described below with reference to the drawings. Note that the dimension, material, and shape of components, the relative arrangement thereof, and the like described below should be changed appropriately depending on the configuration of an apparatus or various conditions to which the invention is applied and are not intended to limit the scope of the invention to the description below.

The present invention has been made for a capacitive transducer for an ultrasound wave and can be applied to an apparatus and an method for transmitting or receiving an ultrasound wave using the transducer. Further, the subject matter of the present invention includes an apparatus utilizing an ultrasound echo technique in which an ultrasound wave is transmitted to an object such as a living body and an echo wave reflected and propagated inside the object is received. By data generation based on the echo wave, characteristic information reflecting the difference in acoustic impedance inside the object can be acquired.

The capacitive transducer of the present invention can be utilized in receiving, besides an echo wave, a photoacoustic wave generated and propagated by a light absorber inside an object through a photoacoustic effect when the object is irradiated with light from a light source. By analyzing the photoacoustic wave, functional information or optical characteristic information relating to the inside of the object can be acquired. Such apparatuses obtain characteristic information by performing analysis with an information processing device after processing by a signal processing unit has been performed with respect to a received echo wave or photoacoustic wave, and therefore can be referred to as object information acquiring apparatus. By displaying the characteristic information as image data in a display unit, internal examination such as a diagnosis is possible.

The present invention can also be understood as a method of controlling an object information acquiring apparatus, an object information acquiring method, or an acoustic wave measurement method. Further, the present invention can also be understood as a program that realizes such a method with an information processing unit such as a CPU or circuit. The present invention can also be understood as a method of manufacturing a capacitive transducer characteristic to the present invention or a method of manufacturing a probe using the same.

In the case of using a capacitive transducer for acquiring characteristic information, use of a probe in which one or a plurality of elements are arranged is preferable. By holding an object for scanning with the probe, measurement over a wide range is possible. If the object is a breast, it is preferable to use, for example, a plate-shaped member or cup-shaped member for holding.

An ultrasound wave referred to in the present invention is given as a typical example of an acoustic wave also called a sound wave or elastic wave. The wavelength or the like is not limited.

An embodiment of the present invention will be described below using FIGS. 1A and 1B. FIG. 1A is a top view of a capacitive transducer of the present invention, and FIG. 1B is a sectional view along line A-B in FIG. 1A. In an element 14 of the capacitive transducer of the present invention, a plurality of cells 12 are formed. The number of elements included in the capacitive transducer is one in FIG. 1A, but may any number. Herein, an element refers to each element of the capacitive transducer of which a signal extraction electrode is shared by all cells forming the element. That is, output of an electrical signal is performed in terms of the elements. The number of cells included in the element 14 is sixty-three in FIG. 1A, but may be any number.

In the cell, a vibrating membrane 9 is supported to be capable of vibration. The vibrating membrane 9 includes a second electrode 1. The second electrode 1 is provided such that a first electrode 2 is across a gap 3 (i.e., cavity). In FIG. 1B, the vibrating membrane has a configuration in which the second electrode 1 is sandwiched between a first membrane 7 and a second membrane 8. However, a configuration with only the second electrode or only the first membrane and the second electrode is acceptable, as long as the vibrating membrane is capable of vibration and includes the second electrode. As will be described later, reference numeral 4 denotes an etching path, reference numeral 6 denotes a sealing portion, reference numeral 10 denotes a substrate, and reference numerals 11 and 15 denote first and second insulating films.

Figure 5:
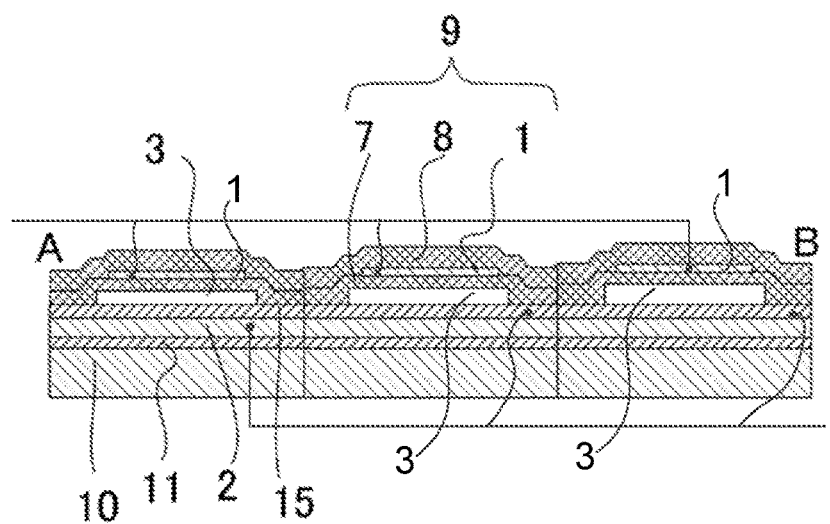
FIG. 5 is a sectional view illustrating connections in certain embodiments.

The first electrode or the second electrode is used as an electrode for applying bias voltage or an electrode for adding an electrical signal or extracting an electrical signal. In this case, the first electrode is used as an electrode for applying bias voltage and the second electrode is used as a signal extraction electrode, but it may be the opposite. The electrode for applying bias voltage is also shared within an element (this is illustrated in FIG. 5, in which the sectional view is along line A-B in FIG. 1A). The configuration may be such that the bias voltage is shared between elements. However, the signal extraction electrode has to be electrically separated for each element.

In the element of the capacitive transducer in FIG. 1A, the gap between cells in an end portion of the element is greater than the gap between cells in a middle portion of the element. It is preferable that the gap between the cells become narrower from the end portion toward the middle portion of the element. It suffices that the gap between a pair of cells in the end portion of the element and the gap between a pair of cells in the middle portion of the element be designed depending on the shape of an intended ultrasound beam. For example, the design may be in accordance with the distribution of a Gaussian beam. Since the density of cells in the end portion of the element is lower than the density of cells in the middle portion of the element, the radiated sound pressure is smaller in the end portion of the element than in the middle portion of the element. Since the density of cells in the end portion of the element is lower than the density of cells in the middle portion of the element, the received sound pressure is smaller in the end portion of the element than in the middle portion of the element in a similar manner.

An ultrasound beam is radiated approximately perpendicularly from the element. This is generally called a main lobe. Further, a side lobe occurs as if to surround the main lobe. The side lobe is stronger when the wavelength of a transmitted or received ultrasound wave is shorter, the size of the element is greater, or the transmission efficiency or receiving sensitivity in the end portion of the element is higher.

Thus, compared to a capacitive transducer having the same transmission efficiency or receiving sensitivity throughout an element from a middle portion to an end portion, a side lobe that occurs on the side of an ultrasound beam can be reduced. Interference by a side lobe can be reduced in a similar manner in the case of reception as well. Therefore, since an ultrasound signal not along the direction of an ultrasound beam and not from a target can be reduced and the S/N ratio of a receive signal can be improved, a high-quality ultrasound image can be formed.

Since the shape of all cells forming the element is the same, the transmission efficiency and the receiving sensitivity of all cells are the same. Therefore, since signals in unnecessary frequency bands are not transmitted or received, deterioration that would otherwise occur in the S/N ratio as a result of such signals can be prevented. The shape of a cell is "the same," i.e., the shape may be exactly the same or may include an error, such as an error due to a manufacturing process, to a degree that the frequency characteristics of the conversion efficiency of a cell can be regarded as being the same.

Since the shape of a vibrating membrane of all cells forming the element is the same, the radiation impedance of all cells is approximately the same. The "radiation impedance" refers to the ratio of force caused by the vibrating membrane pushing an acoustic medium such as liquid and the speed of the vibrating membrane, and shows the radiation capability. Since the radiation impedance of all cells is the same in this configuration, the transmission efficiency and the receiving sensitivity of all cells are approximately the same.

Since the size of a vibrating membrane of all cells within the element can be made the same in this configuration, layout of a cell on a photomask is easy in the case of preparation with a semiconductor manufacturing process. In the case where a gap is 1 μm or less as in this configuration, the etching time for a sacrificial layer depends on the area of the sacrificial layer. Therefore, since the area of a sacrificial layer of all cells is the same in this configuration, the etching time for all cells can be made the same, and a capacitive transducer without a residue of a sacrificial layer and with a small variation in performance can be manufactured.

Further, the configuration may be such that a dummy cell not electrically connected is arranged between active cells and the distances between neighboring cells (distances between overall positions including the active cell position and the dummy cell position) are equal. The active cell is connected to a signal extraction electrode, the active cells are cells electrically connected in parallel (see FIG. 5 for an example), and the dummy cell is a cell that is not electrically connected with the active cell and does not perform transmission or reception of an ultrasound wave. The distances between cells are "the same," i.e., the distance between cells may be exactly the same or may include an error, such as an error due to a manufacturing process, to a degree that the acoustic crosstalk can be regarded as being the same.

The element of the capacitive transducer is formed of a plurality of cells, and the vibrating membrane vibrates in the case where each cell has transmitted or received an ultrasound wave. Due to a sound wave generated by the vibration of the vibrating membrane, acoustic crosstalk occurs between the respective cells. By arranging the dummy cell between the active cells, the acoustic crosstalk of the respective cells can be made approximately the same. Thus, the transmission efficiency and the receiving sensitivity of all cells are approximately the same. Therefore, since signals in unnecessary frequency bands are not transmitted or received, deterioration in the S/N ratio can be prevented.

Further, the configuration may be such that the gaps between all adjacent cells are the same. The transmission efficiency and the receiving sensitivity of all cells of the element of the capacitive transducer of this configuration are the same. Therefore, since signals in unnecessary frequency bands are not transmitted or received, deterioration in the S/N ratio can again be prevented.

The driving principle of the present invention will be described. By using a signal extraction wire, the capacitive transducer can extract an electrical signal from the second electrode. An electrical signal is extracted by an extraction wire in this embodiment, but a through wire or the like may be used. An electrical signal is extracted from the second electrode in this embodiment, but may be extracted from the first electrode.

In the case of receiving an ultrasound wave with the capacitive transducer, a DC voltage is applied to the first electrode 2 by voltage applying means (not shown) to generate a difference in potential between electrodes. In this case, it is recommended that the second electrode 1 be fixed at ground voltage. The ground voltage shows a reference potential in direct current of a current-voltage conversion circuit (receiving circuit) (not shown). When an ultrasound wave is incident, the vibrating membrane 9 including the second electrode 1 is deformed. Therefore, the distance of the gap 3 between the second electrode 1 and the first electrode 2 changes, thereby changing the capacitance. Due to the change in capacitance, current is output from the second electrode 1, and current flows in an extraction wire. The current is converted into voltage by a current-voltage conversion circuit (not shown), and the ultrasound wave can be received. As described above, the configuration of an extraction wire may be changed such that a DC voltage is applied to the second electrode, and an electrical signal is extracted from the first electrode. The current-voltage conversion circuit is preferably provided within a probe 402 in FIG. 4.

In the case of transmitting an ultrasound wave, an AC voltage (including pulse voltage) is applied as a transmission signal to the second electrode 1 in a state where a difference in potential is generated between the first electrode 2 and the second electrode 1, so that the vibrating membrane 9 can be vibrated by the electrostatic force. Accordingly, an ultrasound wave can be transmitted. The configuration of an extraction wire may be changed in the case of transmission as well, such that an AC voltage is applied to the first electrode to vibrate a vibrating membrane.

Using FIGS. 3A to 3E, one form of a preparation method of the this embodiment will be described. FIGS. 3A to 3E are sectional views of a capacitive transducer of the present invention of which the configuration is approximately similar to FIG. 1B. FIGS. 3A to 3E are sectional views along line A-B in FIG. 1A.

Figure 3A:
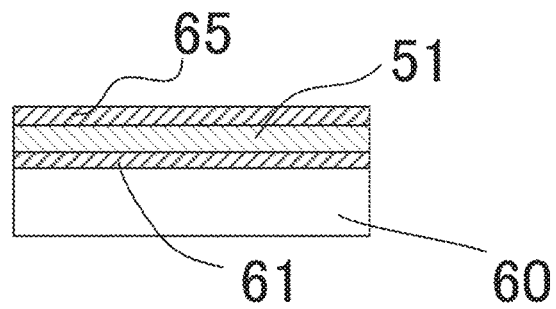
FIGS. 3A to 3E are sectional views along line A-B illustrating a method of preparing a capacitive transducer.

As shown in FIG. 3A, a first insulating film 61 is formed on a substrate 60. The substrate 60 is a silicon substrate, and the first insulating film 61 is provided for insulation from a first electrode. In the case where the substrate 60 is an insulating substrate such as a glass substrate, the first insulating film 61 may not be formed. The substrate 60 is preferably a substrate with a small surface roughness. In the case where the surface roughness is large, the surface roughness is transferred in a membrane forming step that is a step after this step, causing variation among respective cells and respective elements in the distance between the first electrode and a second electrode due to the surface roughness. The variation results in variation in the sensitivity of transmission and reception. Therefore, the substrate 60 is preferably a substrate with a small surface roughness.

Next, a first electrode 51 is formed. For the first electrode 51, a conductive material with a small surface roughness, e.g., titanium or aluminum, is preferable. In the case where the surface roughness of the first electrode is large, variation is caused among respective cells and respective elements in the distance between the first electrode and the second electrode due to the surface roughness in a similar manner to the substrate. Therefore, a conductive material with a small surface roughness is preferable.

Next, a second insulating film 65 is formed. The second insulating film 65 is formed preferably of an insulating material with a small surface roughness in order to prevent an electrical short circuit or dielectric breakdown between the first electrode and the second electrode in the case where voltage is applied between the first electrode and the second electrode. In the case of driving with low voltage, the second insulating film 65 may not be formed, since a first membrane layer described later is an insulator. In the case where the surface roughness of the second insulating film is large, variation is caused among respective cells and respective elements in the distance between the first electrode and the second electrode due to the surface roughness in a similar manner to the substrate. Therefore, a second insulating film with a small surface roughness is preferable. Examples include a silicon nitride film and a silicon oxide film.

Figure 3B:
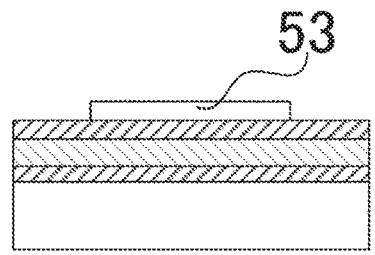

Next, as shown in FIG. 3B, a sacrificial layer 53 is formed. For the sacrificial layer 53, a material with a small surface roughness is preferable. In the case where the surface roughness of the sacrificial layer is large, variation is caused among respective cells and respective elements in the distance between the first electrode and the second electrode due to the surface roughness in a similar manner to the substrate. Therefore, a sacrificial layer with a small surface roughness is preferable. In order to shorten the time for etching in which the sacrificial layer is removed, a material with which the etching speed is fast is preferable.

The material of a sacrificial layer is desired to be such that the second insulating film, the first membrane layer, and the second electrode are almost not etched by etching liquid or etching gas for removing a sacrificial layer. In the case where the second insulating film, the first membrane layer, and the second electrode are nearly etched by etching liquid or etching gas for removing a sacrificial layer, variation in the thickness of a vibrating membrane and variation in the distance between the first electrode and the second electrode occur. The variation in thickness of the vibrating membrane and the variation in the distance between the first electrode and the second electrode become variation in sensitivity among respective cells and among respective elements. In the case where the second insulating film and the first membrane layer are a silicon nitride film or silicon oxide film, chromium with a small surface roughness and for which an etching liquid does not cause etching of the second insulating film, the first membrane layer, and the second electrode is preferable.

With FIGS. 3C to 3E, steps of forming the vibrating membrane including the second electrode and forming a gap through removal of a sacrificial layer will be described. The vibrating membrane is formed of a first membrane, the second electrode, and a second membrane in FIGS. 3A to 3E, but may be formed with any number of layers as long as the second electrode is included.

Figure 3C:
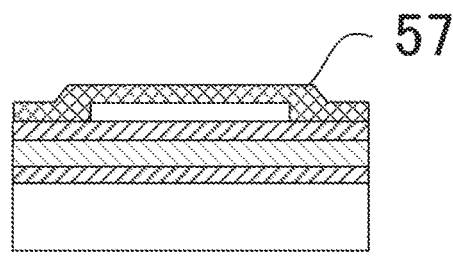

As shown in FIG. 3C, a first membrane layer 57 including the first membrane is formed. For the first membrane layer 57, low tensile stress is preferable. For example, tensile stress of 300 MPa or less is preferable. With a silicon nitride film, control of stress is possible, and the tensile stress can be made 300 MPa or less. In the case where the first membrane has compressive stress, the first membrane becomes highly deformed due to sticking or buckling. In the case of large tensile stress, the first membrane may be broken. Therefore, for the first membrane layer 57, low tensile stress is preferable.

Figure 3D:
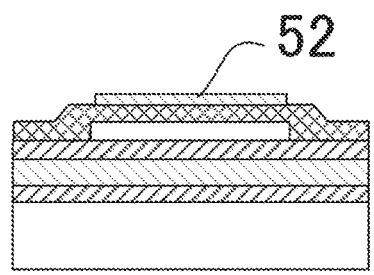

Next, as shown in FIG. 3D, a second electrode 52 is formed, and an etching hole (not shown) is further formed. Then, the sacrificial layer 53 is removed through the etching hole via an etching path (not shown). For the second electrode 52, a material with small residual stress and having heat resistance is preferable. In the case where residual stress of the second electrode is large, the vibrating membrane becomes highly deformed. Therefore, a second electrode with small residual stress is preferable. It is preferable that a material not cause transformation or an increase in stress depending on the temperature or the like upon forming a second membrane layer or a sealing layer for forming a sealing portion.

In the case of performing removal of the sacrificial layer in a state where the second electrode is exposed, etching of the sacrificial layer needs to be performed while a photoresist or the like for protection of the second electrode is applied. Since stress due to the photoresist or the like facilitates sticking of the first membrane, it is preferable that the second electrode have etching resistance such that etching of the sacrificial layer is feasible in a state where the second electrode is exposed without a photoresist. Sticking refers to the adhesion of the vibrating membrane as a structure after removal of the sacrificial layer. For example, titanium, aluminum-silicon alloy or the like is preferable.

Figure 3E:
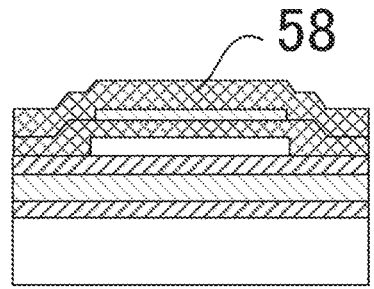

Next, as shown in FIG. 3E, a second membrane layer 58 including the second membrane is formed. In this step, the second membrane is formed, and the sealing portion for sealing the etching hole (not shown) is formed. By forming the second membrane layer 58, the second membrane is formed to form the vibrating membrane having a desired spring constant and enable sealing of the etching hole.

In the case where a step of sealing the etching hole and a step of forming the second membrane are the same as in this step, the vibrating membrane can be formed with only the membrane forming step. Therefore, since it is easy to control the thickness of the vibrating membrane and variation in the spring constant or variation in the deflection of the vibrating membrane due to variation in the thickness can be reduced, variation in the receiving or transmitting sensitivity among cells or elements can be reduced.

The step of sealing the etching hole and the step of forming the second membrane may be separate steps. It may be such that the sealing portion is formed after the second membrane is formed, or the second membrane is formed after the sealing portion is formed.

For the second membrane layer, a material having low tensile stress is preferable. In the case where the second membrane has compressive stress in a similar manner to the first membrane, the first membrane becomes highly deformed due to sticking or buckling. In the case of large tensile stress, the second membrane may be broken. Therefore, for the second membrane layer, low tensile stress is preferable. With a silicon nitride film, control of stress is possible, and the tensile stress can be made 300 MPa or less.

For the sealing portion, it suffices that liquid or external air be prevented from entering into the gap. Particularly, in the case of sealing under reduced pressure, the vibrating membrane is deformed by atmospheric pressure, and the distance between the first electrode and the second electrode decreases. Since the transmitting or receiving sensitivity is proportional to the effective distance between the first electrode and the second electrode raised to the power of 1.5, the transmitting or receiving sensitivity can be improved through sealing under reduced pressure such that the pressure in the gap is lower than the atmospheric pressure. The effective distance takes into consideration the gap and a value for the insulating film for the first electrode and the second electrode obtained through division by the dielectric constant.

After this step, a wire connecting the first electrode and the second electrode is formed by a step that is not shown. The material for the wire may be aluminum or the like.

With such a manufacturing method, a capacitive transducer having a configuration necessary for achieving the object of the present invention can be manufactured.

A more specific example will be given below for a detailed description of the present invention.

Example 1

An embodiment of the present invention will be described below using FIGS. 1A and 1B. FIG. 1A is a top view of the capacitive transducer of the present invention, and FIG. 1B is a sectional view along line A-B in FIG. 1A. The element 14 of the capacitive transducer of the present invention is formed of sixty-three cells 12. The number of elements included in the capacitive transducer is one in FIG. 1A, but may any number.

The cell 12 is supported such that the vibrating membrane 9 including the second electrode 1 provided across the gap 3 from the first electrode 2 is capable of vibration. The vibrating membrane 9 has a configuration in which the second electrode 1 is sandwiched between the first membrane 7 and the second membrane 8. The first electrode 2 is an electrode for applying bias voltage, and the second electrode 1 is a signal extraction electrode. The shape of the vibrating membrane in this example is a circle. However, the shape may be a quadrangle, hexagon, or the like. In the case of a circle, the vibrational mode is axisymmetric. Therefore, vibration of the vibrating membrane due to an unnecessary vibrational mode can be reduced.

The first insulating film 11 on the silicon substrate 10 is a silicon oxide film formed by thermal oxidation and with a thickness of 1 µm. The second insulating film 15 is a silicon oxide film formed by plasma-enhanced chemical vapor deposition (PE-CVD) and with a thickness of 0.1 µm. The first electrode is aluminum with a thickness of 50 nm, and the second electrode 1 is aluminum with a thickness of 100 nm. The first membrane 7 and the second membrane 8 are silicon nitride films prepared by PE-CVD and are formed with tensile stress of 200 MPa or less. The diameter of the first membrane 7 and the second membrane 8 is 25 µm. The respective thicknesses are 0.4 µm and 0.7 µm.

In the element of the capacitive transducer in FIG. 1A, the gap between cells in the end portion of the element is greater than the gap between cells in the middle portion of the element. Since the density of cells in the end portion of the element is lower than the density of cells in the middle portion of the element, the radiated sound pressure is smaller in the end portion of the element than in the middle portion of the element. Since the density of cells in the end portion of the element is lower than the density of cells in the middle portion of the element, the received sound pressure is smaller in the end portion of the element than in the middle portion of the element in a similar manner. Thus, compared to a capacitive transducer having the same transmission efficiency or receiving sensitivity throughout an element from a middle portion to an end portion, a side lobe that occurs on the side of an ultrasound beam can be reduced. Therefore, an ultrasound signal not along the direction of an ultrasound beam and not from a target can be reduced, and a high-quality ultrasound image can be formed. Since the shape of all cells forming the element is the same, the transmission efficiency and the receiving sensitivity of all cells are the same. Therefore, since a signal in an unnecessary frequency band is not transmitted or received, deterioration in the S/N ratio can be prevented.

Since the shape of a vibrating membrane of all cells forming the element is the same, the radiation impedance of all cells is approximately the same. Since the radiation impedance of all cells is the same in this configuration, the transmission efficiency and the receiving sensitivity of all cells are approximately the same.

Since the size of a vibrating membrane of all cells within the element can be made the same in this configuration, layout of a cell on a photomask is easy in the case of preparation with a semiconductor manufacturing process. In the case where the gap is 1 µm or less as in this configuration, the etching time for a sacrificial layer depends on the area of the sacrificial layer. Therefore, since the area of a sacrificial layer of all cells is the same in this configuration, the etching time for all cells can be made the same, and a capacitive transducer without a residue of a sacrificial layer and with a small variation in performance can be manufactured.

The shape of a vibrating membrane of a cell is the same within the element, and only the arrangement of a cell when seen from above is not uniform. Thus, in the case of preparing the capacitive transducer of the present invention using a semiconductor manufacturing process, preparation is feasible with the same manufacturing method as for a capacitive transducer in which the cell arrangement is uniform.

Example 2

The configuration of a capacitive transducer of Example 2 will be described using FIGS. 2A and 2B. FIG. 2A is a top view of the capacitive transducer of the present invention. Example 2 is approximately similar to Example 1 in the configuration of the capacitive transducer. Thus, the differences will be mainly described.

The capacitive transducer in FIGS. 2A and 2B includes a second electrode 21, a first electrode 22, a gap 23, a sealing portion 26, a first membrane 27, a second membrane 28, a vibrating membrane 29, a substrate 30, a first insulating film 31, a cell 32, an element 34, and a second insulating film 35.

In the element of the capacitive transducer in FIG. 2A, the configuration is such that a dummy cell not electrically connected is arranged between active cells. The distances between neighboring cells (distances between cell positions, in the case where a cell position is taken in the broad sense to include the active cell position and the dummy cell position) are equal. The active cell is connected to a signal extraction electrode, the active cells are cells electrically connected in parallel, and the dummy cell is a cell that is not electrically connected with the active cell and does not perform transmission or reception of an ultrasound wave.

In the case of this example, the gaps between cells (in the broad sense), in the case where a cell is considered in the broad sense to include the active cell and the dummy cell, are equal. In the case where a cell is considered in the narrow sense as only the active cell (relating to ultrasound wave transmission or reception), the gap between cells (in the narrow sense) depends on the position of the element. For example, in FIG. 2A, the active cells are adjacent in a middle portion of the element such as in the sixth to eighth rows from the top, and the gap between the cells (in the narrow sense) is relatively narrow. Toward the end portion of the element, the dummy cell is arranged in the second and ninth rows, and the gap between the neighboring cells (in the narrow sense) is large.

The element of the capacitive transducer is formed of a plurality of cells, and the vibrating membrane vibrates in the case where each cell has transmitted or received an ultrasound wave. Due to a sound wave generated by the vibration of the vibrating membrane, acoustic crosstalk occurs between the respective cells. With a configuration in which the dummy cell is arranged between the active cells and all distances between the cells (in the broad sense) are equal, the acoustic crosstalk of the respective cells can be made the same. Thus, the transmission efficiency and the receiving sensitivity of all cells are approximately the same. Therefore, since a signal in an unnecessary frequency band is not transmitted or received, deterioration in the S/N ratio can be prevented.

In the capacitive transducer according to the present invention, the gap between cells in the end portion of the element is greater than the gap between cells in the middle portion of the element, as described above. Since the density of cells in the end portion of the element is lower than the density of cells in the middle portion of the element, the radiated sound pressure is smaller in the end portion of the element than in the middle portion of the element. Since the density of cells in the end portion of the element is lower than the density of cells in the middle portion of the element, the received sound pressure is smaller in the end portion of the element than in the middle portion of the element in a similar manner.

Thus, compared to a capacitive transducer having the same transmission efficiency or receiving sensitivity throughout an element from a middle portion to an end portion, a side lobe that occurs on the side of an ultrasound beam can be reduced. Interference by a side lobe can be reduced in a similar manner in the case of reception as well. Therefore, since an ultrasound signal not along the direction of an ultrasound beam and not from a target can be reduced and the S/N ratio of a receive signal can be improved, a high-quality ultrasound image can be formed. Since the shape of all cells forming the element is the same, the transmission efficiency and the receiving sensitivity of all cells are the same. Therefore, since a signal in an unnecessary frequency band is not transmitted or received, deterioration in the S/N ratio can be prevented.

Application Example

The capacitive transducer described above can be applied to a probe that receives or transmits an acoustic wave using the same. For example, in FIG. 4, the probe 402 includes a plurality of elements 403. By a transmission unit 405 performing control of a transmitted acoustic wave according to a command by an information processing unit 406, an acoustic wave is generated from each element. At the time of reception, an electrical signal output from each element is subjected to processing (e.g., amplification or AD conversion) by a signal processing unit 404.

FIG. 4 shows the probe described above being used as a component of an object information acquiring apparatus.

First, a case where a light absorber inside an object 401 absorbs light from a light source (not shown) to generate a photoacoustic wave will be described. At this time, the photoacoustic wave propagates inside the object and is received by the element. An electrical signal output from the element is input to the signal processing unit and subjected to signal processing. Based on a signal input from the signal processing unit, the information processing unit generates as characteristic information initial sound pressure distribution, absorption coefficient distribution, or the like of the inside of the object by known image reconstruction processing. Upon diagnosis, such information may be displayed in a display unit 407 as image data according to necessity. In this specification, a configuration formed of the signal processing unit and the information processing unit may be referred to as processing unit.

Next, a case of acquiring echo information relating to the inside of an object will be described. With a control signal sent by the transmission unit at this time, an acoustic wave is transmitted from each element. The acoustic wave reflected at the acoustic impedance boundary inside the object is received again by the element. A receive signal output from the element is subjected to known signal processing, reconstruction processing, or image data generation, in a similar manner to the case of a photoacoustic wave. In the case of an apparatus using the reflected wave, a probe for transmission of an acoustic wave may be provided separately from a probe for reception.

Further, the capacitive transducer of the present invention can be applied to an apparatus having both functions as an apparatus using a photoacoustic wave and an apparatus using an echo wave.

The probe may be for mechanical scanning or may be a probe (of a handheld type) that is grasped by a user such as a doctor or technician and moved with respect to an object. Particularly in the case of mechanically scanning an object that is a living body, stable measurement is made possible by holding the object with holding means. If the object is a breast, a plate-shaped or cup-shaped holding means is suitable.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-092668, filed on Apr. 25, 2013, and Japanese Patent Application No. 2014-022480, filed on Feb. 7, 2014, which are hereby incorporated by reference herein in their entirety.

What is claimed is:

1. A capacitive transducer comprising:
    an element including a plurality of cells, the element having an end portion and a middle portion, and having at least two of the cells in the end portion and at least two of the cells in the middle portion,
    wherein each cell includes a vibrating membrane that is connected to one of a first electrode and a second electrode,
    wherein there is a gap between the first electrode and the second electrode,
    wherein an electrical signal is outputted via either one of the first electrode and the second electrode when an acoustic wave from an object is incident on the vibrating membrane and the vibrating membrane vibrates,
    wherein the cells in the end portion of the element have a diameter equal to that of the cells in the middle portion of the element,
    wherein the first electrodes of all cells in the element are electrically connected to each other, and the second electrodes of all cells in the element are electrically connected to each other, and
    wherein shape of the element is rectangular having a pair of long sides and a pair of short sides; in a direction along the long side, the distance between cells in the end portion of the element is greater than the distance between cells in the middle portion of the element; and in a direction along the short side, the distance between cells in the end portion of the element is equal to the distance between cells in the middle portion of the element.

2. The capacitive transducer according to claim 1, wherein the plurality of cells includes active cells and dummy cells, wherein the active cells are electrically connected to the second electrode in parallel, and the dummy cells are not electrically connected to the active cells.

3. The capacitive transducer according to claim 2, wherein a distance between two adjacent active cells of the plurality of cells is equal to a distance between two adjacent dummy cells of the plurality of cells.

4. A probe comprising a capacitive transducer according to claim 1.

5. An object information acquiring apparatus comprising:
    a capacitive transducer according to claim 1; and
    a processing unit which acquires characteristic information relating to an inside of the object by using the electrical signal.

6. The object information acquiring apparatus according to claim 5, further comprising a transmission unit with which the vibrating membrane is vibrated by applying voltage to the first and the second electrodes to cause transmission of an acoustic wave to the object,
wherein the acoustic wave is a reflection of the transmitted acoustic wave from the inside of the object.

7. The object information acquiring apparatus according to claim 5, further comprising a light source,
wherein the acoustic wave is a photoacoustic wave generated from the object irradiated with light from the light source.

8. The object information acquiring apparatus according to claim 5,
wherein a common bias voltage is applied to each of the cells in the element.

9. The object information acquiring apparatus according to claim 5,
wherein the cells of the element each have the same shape.

10. The object information acquiring apparatus according to claim 5,
wherein the object information acquiring apparatus comprises a plurality of the elements, and
wherein a common bias voltage is applied to each of the plurality of the elements.

11. The capacitive transducer according to claim 2, wherein a shape of the dummy cells and a shape of the active cells are the same.

12. The capacitive transducer according to claim 1, wherein the sizes of all cells in each element are uniform.

* * * * *